US00PP18615P2

(12) United States Plant Patent
Takamura

(10) Patent No.: US PP18,615 P2
(45) Date of Patent: Mar. 18, 2008

(54) *VERBENA* PLANT NAMED 'SUNMARIRED'

(50) Latin Name: *Verbena hybrida*
Varietal Denomination: Sunmarired

(75) Inventor: Naoto Takamura, Yamanashi (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 11/527,822

(22) Filed: Sep. 27, 2006

(51) Int. Cl.
*A01H 5/00* (2006.01)

(52) U.S. Cl. ..... Plt./308
(58) Field of Classification Search ..... Plt./308
See application file for complete search history.

(56) References Cited

U.S. PATENT DOCUMENTS

PP10,311 P * 3/1998 Tachibana ..... Plt./308
PP17,922 P2 * 8/2007 Dummen ..... Plt./208
2007/0209095 P1 * 9/2007 Stemkens ..... Plt./308

OTHER PUBLICATIONS

UPOV ROM GTITM Computer Database, GTI Jouve Retrieval Software 2007/02 Citation for 'Sunmarired'.*

* cited by examiner

*Primary Examiner*—Wendy Haas
(74) *Attorney, Agent, or Firm*—C. A. Whealy

(57) ABSTRACT

A new and distinct cultivar of *Verbena* plant named 'Sunmarired', characterized by its outwardly spreading to trailing plant habit; vigorous growth habit; freely branching habit; freely flowering habit; and intense red-colored flowers that are held above and beyond the foliage.

1 Drawing Sheet

Botanical designation: *Verbena hybrida.*
Cultivar denomination: 'Sunmarired'.

BACKGROUND OF THE INVENTION

The present invention relates to a new and distinct cultivar of *Verbena,* botanically known as *Verbena hybrida,* and hereinafter referred to by the name 'Sunmarired'.

The new *Verbena* is a product of a planned breeding program conducted by the Inventor in Higashiomi, Shiga, Japan. The objective of the breeding program is to create new *Verbena* cultivars with large inflorescences and attractive flower coloration.

The new *Verbena* originated from a cross-pollination made by the Inventor in June, 2002 in Higashiomi, Shiga, Japan of a proprietary seedling selection of *Verbena hybrida* identified as code number USV65, not patented, as the female, or seed, parent with a proprietary seedling selection of *Verbena hybrida* identified as code number H232-2, not patented, as the male, or pollen, parent. The new *Verbena* was discovered and selected by the Inventor as a single flowering plan within the progeny of the stated cross-pollination in a controlled environment in Higashiomi, Shiga, Japan.

Asexual reproduction of the new *Verbena* by terminal cuttings in a controlled environment in Higashiomi, Shiga, Japan since October, 2003 has shown that the unique features of this new *Verbena* are stable and reproduced true to type in successive generations.

SUMMARY OF THE INVENTION

The cultivar Sunmarired has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunmarired'. These characteristics in combination distinguish 'Sunmarired' as a new and distinct cultivar of *Verbena:*

1. Outwardly spreading to trailing plant habit.
2. Vigorous growth habit.
3. Freely branching habit.
4. Freely flowering habit.
5. Intense red-colored flowers that are held above and beyond the foliage.

Plants of the new *Verbena* can be compared to plants of the female parent selection. Plants of the new *Verbena* differ from plants of the female parent selection in the following characteristics:

1. Plants of the new *Verbena* are broader than plants of the female parent selection.
2. Plants of the new *Verbena* have shorter internodes than plants of the female parent selection.
3. Plants of the new *Verbena* have larger flowers than plants of the female parent selection.

Plants of the new *Verbena* can be compared to plants of the male parent selection. Plants of the new *Verbena* differ from plants of the male parent selection in the following characteristics:

1. Plants of the new *Verbena* are more trailing than and not as upright as plants of the male parent selection.
2. Plants of the new *Verbena* are broader than plants of the male parent selection.
3. Plants of the new *Verbena* and the male parent selection differ in flower color as plants of the male parent selection have pink-colored flowers.

Plants of the new *Verbena* can be compared to plants of the *Verbena* cultivar Sunvp-su, disclosed in U.S. Plant Pat. No. 10,311. In side-by-side comparisons conducted in Higashiomi, Shiga, Japan, plants of the new *Verbena* differed from plants of the cultivar Sunvp-su in the following characteristics:

1. Plants of the new *Verbena* were not as broad as plants of the cultivar Sunvp-su.
2. Plants of the new *Verbena* had larger flowers than plants of the cultivar Sunvp-su.
3. Plants of the new *Verbena* had broader petals than plants of the cultivar Sunvp-su.
4. Plants of the new *Verbena* and the cultivar Sunvp-su differed in flower color as plants of the cultivar Sunvp-su had lighter red-colored flowers.
5. Plants of the new *Verbena* had thicker peduncles than plants of the cultivar Sunvp-su.

BRIEF DESCRIPTION OF THE PHOTOGRAPHS

The accompanying colored photographs illustrate the overall appearance of the new *Verbena*, showing the colors as true as it is reasonably possible to obtain in colored reproductions of this type. Colors in the photographs may differ slightly from the color values cited in the detailed botanical description which accurately describe the colors of the new *Verbena*.

The photograph at the top of the sheet comprises a side perspective view of a typical flowering plant of 'Sunmarired' grown in a container.

The photograph at the bottom of the sheet is a close-up view of a typical inflorescence of 'Sunmarired'.

DETAILED BOTANICAL DESCRIPTION

The aforementioned photographs and following observations and measurements describe plants grown in Higashiomi, Shiga, Japan, under commercial practice during the summer in an outdoor nursery with day temperatures averaging 21° C. and night temperatures averaging 14° C. Plants were grown with one rooted cutting per 13.5-cm container for about four months. In the following description, color references are made to The Royal Horticultural Society Colour Chart, 2001 Edition, except where general terms of ordinary dictionary significance are used.

Botanical classification: *Verbena hybrida* cultivar Sunmarired.

Parentage:

*Female, or seed, parent.*—Proprietary seedling selection of *Verbena hybrida* identified as code number USV65, not patented.

*Male, or pollen, parent.*—Proprietary seedling selection of *Verbena hybrida* identified as code number H232-2, not patented.

Propagation:

*Type.*—By terminal cuttings.

*Time to initiate roots.*—About 10 to 14 days at 20° C. to 25° C.

*Time to produce a rooted young plant.*—About four weeks at 20° C. to 25° C.

*Root description.*—Fine, fibrous; ivory to pale brown in color.

*Rooting habit.*—Freely branching.

Plant description:

*Plant habit.*—Initially upright, then outwardly spreading to trailing growth habit; lateral branches decumbent. Freely branching habit with about 17 to 18 primary lateral branches developing per plant; pinching enhances lateral branch development. Vigorous growth habit.

*Plant height.*—About 15.3 cm.

*Plant diameter.*—About 50.4 cm.

Lateral branch description:

*Length.*—About 20.2 cm.

*Diameter.*—About 2.3 mm.

*Internode length.*—About 6.3 cm.

*Strength.*—Strong.

*Texture.*—Pubescent.

*Color.*—144A.

Foliage description:

*Arrangement.*—Opposite, simple.

*Length.*—About 5.5 cm.

*Width.*—About 2.7 cm.

*Shape.*—Narrowly ovate.

*Apex.*—Acute.

*Base.*—Truncate.

*Margin.*—Serrate.

*Texture, upper and lower surfaces.*—Coarse, rough; pubescent.

*Venation pattern.*—Pinnate; reticulate.

*Color.*—Developing and fully expanded foliage, upper surface: 137A; venation, 145B. Developing and fully expanded foliage, lower surface: 137C; venation, 145B.

*Petiole: Length: About* 1.1 cm. Diameter: About 1.2 mm. Texture, upper and lower surfaces: Pubescent. Color, upper and lower surfaces: 145A.

Flower description:

*Flower arrangement and habit.*—Salverform flowers arranged in hemispherical terminal racemes; flowers face upward or outward. Freely flowering habit with about 20 flowers per inflorescence.

*Natural flowering season.*—Plants flower continuously from spring to late autumn in Japan.

*Flower longevity.*—Flowers last about one week on the plant. Flowers not persistent.

*Fragrance.*—None detected.

*Inflorescence height.*—About 2.9 cm.

*Inflorescence diameter.*—About 6.2 cm.

*Flowers.*—Appearance: Flared trumpet, corolla fused, five-parted. Diameter: About 2.2 cm. Depth (height): About 2.3 cm. Throat diameter: About 2.1 mm.

*Flower buds.*—Length: About 2.4 cm. Diameter: About 4.2 mm. Shape: Clavate. Color: 45A.

*Corolla.*—Arrangement: Single whorl of five fused petals. Petal length: About 1.1 cm. Petal width: About 1.1 cm. Petal lobe shape: Obcordate. Petal lobe apex: Cordate. Petal margin: Entire. Petal texture, upper and lower surfaces: Smooth, glabrous; velvety. Color: Petal, when opening and fully opened, upper surface: 45B; towards the throat, 46A. Petal, when opening and fully opened, lower surface: 45D. Throat: 145D. Tube: 145D.

*Calyx.*—Arrangement: One single narrow calyx tube per flower with five fused sepals. Sepal length: About 1.3 cm. Sepal width: About 1 mm. Sepal shape: Lanceolate. Sepal apex: Acute. Sepal margin: Entire. Sepal texture, upper surface: Smooth, glabrous. Sepal texture, lower surface: Pubescent. Sepal color, upper and lower surfaces: 137C.

*Peduncles.*—Length: About 6.6 cm. Diameter: About 1.8 mm. Strength: Strong. Texture: Pubescent. Color: 144A.

*Pedicels.*—Flowers are sessile.

*Reproductive organs.*—Stamens: Quantity/arrangement: Four per flower, adnate to corolla tube. Anther shape: Ellipsoidal. Anther length: About 1 mm. Anther color: 145B. Pollen amount: Scarce.

Pollen color: 10D. Pistils: Quantity: One per flower. Pistil length: About 1.9 cm. Stigma shape: Bi-parted. Stigma color: 144B. Style color: 144C. Ovary color: 144A. Fruits/seed: Fruit and seed development have not been observed.

Temperature tolerance: Plants of the new *Verbena* have been observed to tolerate temperatures from about 0° C. to about 35° C.

Pathogen/pest resistance: Plants of the new *Verbena* have not been observed to be resistant to pathogens and pests common to *Verbenas*.

It is claimed:

1. A new and distinct *Verbena* plant named 'Sunmarired' as illustrated and described.

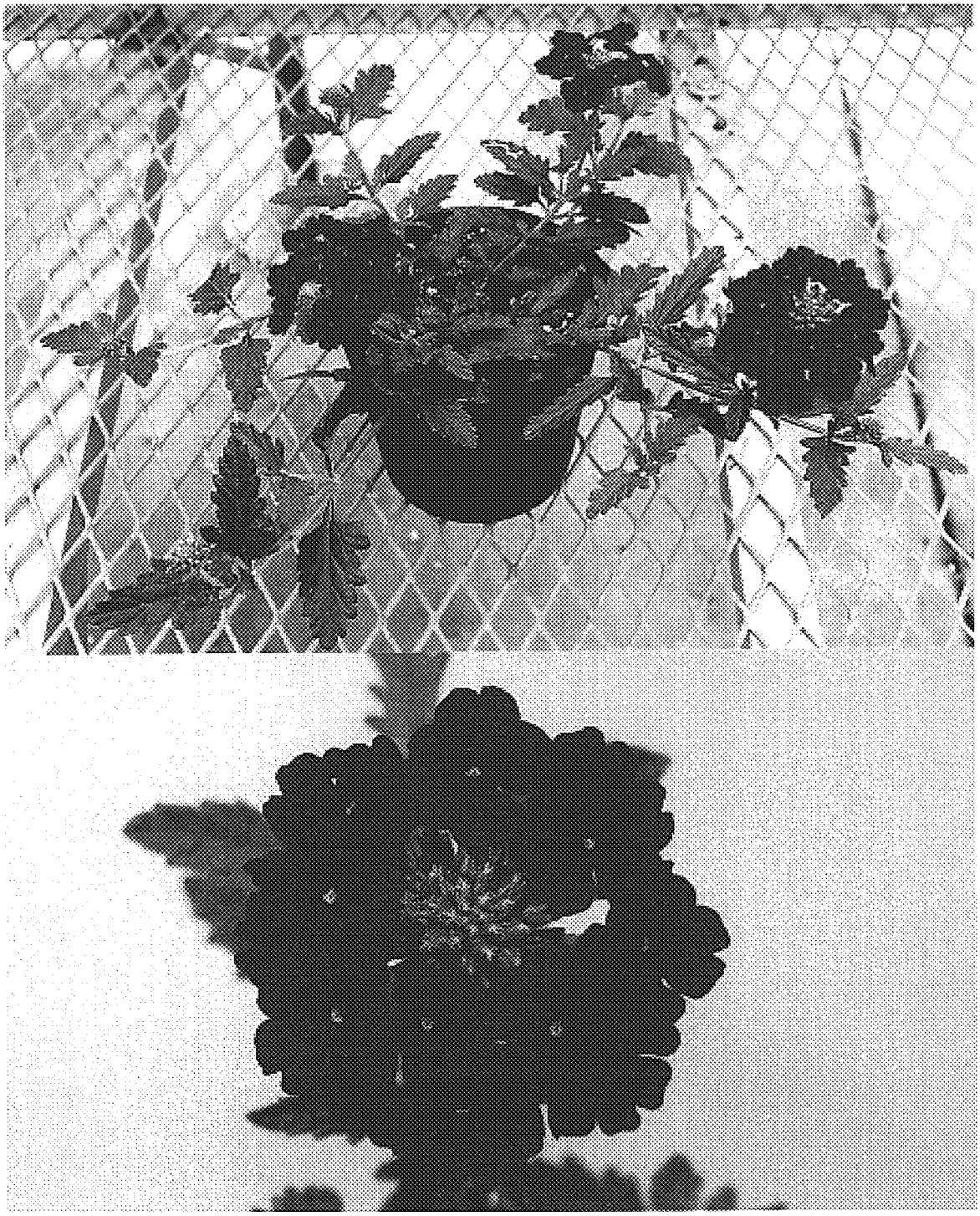

* * * * *